United States Patent [19]

Grassberger et al.

[11] Patent Number: 5,665,727
[45] Date of Patent: Sep. 9, 1997

[54] USE OF 11,28-DIOXA-4-AZATRICYCLO [22.3.1.0^{4,9}]OCTACOS-18-ENE DERIVATIVES AND PHARMACEUTICAL COMPOSITIONS CONTAINING THEM

[75] Inventors: Maximilian Grassberger, Vienna; Josef Gottfried Meingassner, Perchtoldsdorf; Anton Stütz; Peter Stütz, both of Vienna, all of Austria

[73] Assignee: Sandoz Ltd., Basel, Switzerland

[21] Appl. No.: 291,010

[22] Filed: Aug. 15, 1994

Related U.S. Application Data

[62] Division of Ser. No. 982,925, Nov. 30, 1992, Pat. No. 5,366,971, which is a continuation of Ser. No. 608,430, Nov. 2, 1990, abandoned, which is a continuation of Ser. No. 268,114, Nov. 7, 1988, abandoned.

[30] Foreign Application Priority Data

Nov. 9, 1987 [AT] Austria ................................. 2952/87
Dec. 17, 1987 [DE] Germany ........................ 37 42 805.5

[51] Int. Cl.$^6$ ........................... A61K 31/44; A61K 31/40
[52] U.S. Cl. ................................... 514/291; 514/411
[58] Field of Search ............................... 514/291, 411

[56] References Cited

U.S. PATENT DOCUMENTS 4,139,563  2/1979  Metcalf et al. ..................... 260/583 H

FOREIGN PATENT DOCUMENTS

| 0090378 | 10/1983 | European Pat. Off. . | |
|---|---|---|---|
| 0127425 | 12/1984 | European Pat. Off. . | |
| 0147476 | 7/1985 | European Pat. Off. . | |
| 0240773 | 4/1986 | European Pat. Off. . | |
| 0184162 | 6/1986 | European Pat. Off. . | |
| 184162 | 6/1986 | European Pat. Off. | 514/291 |
| WO8607359 | 12/1986 | WIPO . | |

OTHER PUBLICATIONS

Chem. Abstract, vol. 93, 1981, 197620t.
Chem. Abstract, vol. 94, 1981, 150,334s.
Chem. Abstract, vol. 78, 1973, 92678p.
Chem. Abstract, vol. 86, 1977, 37594y.
Chem. Abstract, vol. 78, 1973, 69958w.
Chem. Abstract, vol. 70, 1969, 113403x.
Chem. Abstract, vol. 84, 1976, 130015d.
Chem. Abstract, vol. 71, 1969, 59514q.
Script No. 1717 (May 13, 1987).
Arch. Derm. 123, 165–166 (1987).
J. Invest. Derm. 88 52–54 (1987).
Transplan. 44, 83–87 (1987).
The Lancet, Apr. 4, 1987—p. 806.
Surgical Forum, vol. 37, 1986, pp. 603–604.
J. Am. Acad. Dermatol 14:785–791 (1986).
Clin. Exp. Immunol. 66, 582–589 (1986).
Clinical Research, vol. 34, No. 4, 1986—p. 1007A.
The Lancet, Oct. 4, 1986—pp. 803–804.
Lancet 1986/II, pp. 971–972.
The Lancet, Jan. 19, 1985—p. 160.
Clin. Exp. Immunol. 59, 23–28 (1985).
New Engl. J. Med. 301, 555 (1979).
Clin. Exp. Immunol. 45, 173–177 (1981).
Transplan. Proc. vol. XV, No. 4, Suppl. 1 (1983) pp. 3084–3085 and 3091.
Arch. Derm. 122, 1028–1032 (1986).
Clin. Exp. Immunol. (1985) 59, 23–28.
J. Org. Chem. 1985, 50, 2582–2583.
Chemical Abstracts, vol. 104, 1986.
J. Invest. Derm. 82, 419 (1984).
Clin. Res. 1986, 34, 1007A.
The Lancet, vol. 339, May 2, 1992, p. 1120.
Transplan. Proc. vol. XIX, No. 5, 1987: pp. 79–83, Suppl. 8.
Transplan. Proc. (1987), vol. XIX, No. 5, Supply. 6, pp. 40–44.
The Journal of Antibiotics, vol. XL No. 9—pp. 1249–1255, Sep. 1987.
The Journal of Antibiotics, vol. XL, No. 9 (1987), Index, pp. 1256–126.
J. Am. Chem. Soc. 1987, 109, 5031–5033.
Chemical Abstracts—vol. 107, No. 3, 1987, 17437y.
Transplan. Proc. vol. XIX, No. 5, Supply 6, (1987) pp. 84–86.
Dermatology in General Medicine, 3rd Edition, 1987.
Arch. Dermatol Res (1983) 275: 181–189.
J. Allergy Clin. Immol. vol. 71, No. 1, Part 1, pp. 47–56.
Contact Dermatitis vol. 19, pp. 129–132 (1988).

*Primary Examiner*—Jerome D. Goldberg
*Attorney, Agent, or Firm*—Robert S. Honor; Melvyn M. Kassenoff; Thomas O. McGovern

[57] ABSTRACT

The compounds of formula I,

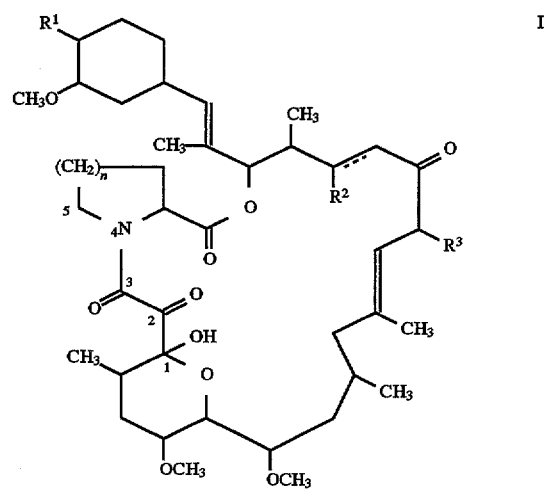

have been found to have excellent topical activity. They are thus indicated for use in the topical treatment of inflammatory and hyperpoliferative skin diseases and of cutaneous manifestations of immunologically-induced illnesses, such as psoriasis.

18 Claims, No Drawings

USE OF 11,28-DIOXA-4-AZATRICYCLO [22.3.1.0⁴,⁹]OCTACOS-18-ENE DERIVATIVES AND PHARMACEUTICAL COMPOSITIONS CONTAINING THEM

This is a division of application Ser. No. 07/982,925, filed Nov. 30, 1992, now U.S. Pat. No. 5,366,971, issued Nov. 22, 1994, which in turn is a continuation of application Ser. No. 07/608,340, filed Nov. 2, 1990, which in turn is a continuation of application Ser. No. 07/268,114, filed Nov. 7, 1988, the latter two of which are now abandoned.

The invention concerns a new use of the compounds of formula I,

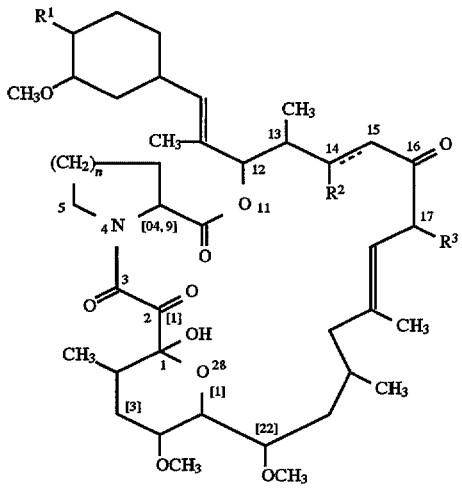

wherein
$R^1$ is optionally protected hydroxy,
$R^2$ is hydrogen or optionally protected hydroxy,
$R^3$ is methyl, ethyl, propyl or allyl,
n is 1 or 2 and
the symbol of a line and dotted line is single bond or a double bond,
in free form or in salt form,
in the topical treatment of inflammatory and hyperproliferative skin diseases and of cutaneous manifestations of immunologically-mediated illnesses, such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneohs eosinophilias, Lupus erythematosus and Alopecia areata.

The compounds of formula I, their preparation and their immunosuppressant and antimicrobial activity are described in e.g. Fujisawa EP 184 162.

It has now been found that the compounds of formula I possess further interesting pharmacological properties which make them indicated for further uses as pharmaceuticals.

It is known and has been repeatedly published in the literature that cyclosporin A (Sandimmun®), a highly active immunosuppressant, has practically no activity upon topical administration in e.g. psoriasis (Lancet [1987] p. 806; J. Invest. Dermatol. 90 [1988] 251). In animal testing for contact allergies in mice and guinea pigs cyclosporin A is only active upon topical administration of compositions containing at least 0.1%, and in the pig cyclgsporin A is inactive in compositions with up to 5% cyclosporin A.

It has now been found that surprisingly, the compounds of formula I have an excellent topical activity. They are thus very effective in pigs when administered topically against DNFB contact allergies. In mice with oxazolone allergy a superiority by a factor of at least 25 over cyclosporin A is found. Further, the compounds of formula I also exhibit an antiinflammatory effect upon topical administration in animal models of dermatitis caused by irritants. This is indicative of a general antiinflammatory activity upon epicutaneous application. This is corroborated by results from investigations in vitro: inhibition of TPA-induced $PGE_2$ release from macrophages, and inhibition of FMLP- and, respectively, calcium ionophor A 23187-stimulated oxidative burst of human neutrophil polymorphonucleated leukocytes. The compounds of formula I further exhibit an inhibitory effect in cell culture on the proliferation of human keratinocytes.

The compounds of formula I in free form or in pharmaceutically acceptable salt form are therefore useful upon topical administration in the therapy of inflammatory and hyperproliferative skin diseases and of cutaneous manifestations of immunologically-mediated illnesses, such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and Alopecia arcata.

These activities are apparent in the following test systems:
1. Determination of the activity after topical administration in models of allergic or allergen-induced contact dermatitis (DTH-reaction)
    1.1. Oxazolone allergy (mouse):

10 μl of a 2% oxazolone solution are applied onto the abdominal skin of mice for sensitization. 8 days later a second exposure with 10 μl of a 2% oxazolone solution is performed by application on the peripheral internal surface of the pinna. 20 minutes and 2 hours after the second exposure has released the challenge reaction, the test solution is applied at the site of the second exposure. Evaluation of the inhibition of inflammation with the test substance is effected by reference to an untreated group treated with the solvent used for dissolving the test substance, alone. 24 hours after the second exposure the animals are killed and the separated pinnae are weighted. The difference in weight between the two pinnae is used for evaluation; the individual differences in the test group and in the solvent control group are statistically compared (by simple variance analysis with subsequent Dunnet test by normal distribution test if normally distributed, otherwise by Kruskal-Wallis' U-test and Wilcoxon-Mann-Whitney's U-test). The activity of the test substance is indicated in %, based on mean values.

Table 1 shows the results obtained in this model for compounds of formula I and cyclosporin A. Ethanol is used as solvent.

TABLE 1

| Substance | % concentration | % inhibition |
|---|---|---|
| A | 0.13 | 65 |
|   | 0.01 | 65 |
|   | 0.005 | 52 |
|   | 0.002 | 38 |
|   | 0.0005 | 35 |
| B | 0.005 | 60 |
| Cyclosporin A | 0.4 | 71 |
|   | 0.13 | 56 |
|   | 0.04 | 28 |
|   | 0.01 | 15 |

1.2. DNFB allergy (swine):

The use of dinitrofluorobenzene (DNFB) or dinitrochlorobenzene (DNCB) for inducing a contact allergy is a classical experimental approach which is also being used in humans (P. S. Friedmann and C. Moss, *Models in Dermatology* [1987] Maibach, Lowe, Ed., Vol. 2, p. 275–281, Karger-Basel). In view of the resemblance between porcine and human skin a corresponding model for topical testing of substances is built up in the swine. On the 1st and 3rd day 100 µl each of a 10% DNFB preparation is applied onto the inner surface of the right and, respectively, left thigh. On the 14th day each swine is marked on the right and the left side of the back with circular markings of 5 cm in diameter (8 markings per animal) and 150 µl each of a 0.5% DNFB preparation is applied thereon. The substances are tested either in the form of galenical compositions or of a solution. The carriers are used in each case as placebo controls.

The test products are carefully applied 4 times (first 30 minutes, then 6, 24 and 32 hours after release of the challenge reaction). Prior to each application the test areas are evaluated with respect to reddenning, swelling and consistance. The coloration of the test areas is then determined quantitatively with a reflectometer, repeatedly. From the data on brightness (L*) and saturation (C*) the erythema index is computed according to the following formula: 100−L*×C*. The mean erythema index is a reflection of the activity according to the following formula:

$$\frac{\% \text{ inhibition}}{(24, 32, 48, 56 \text{ hours})} = 100 - \frac{\text{delta (placebo)} - \text{delta (test)}}{\text{delta (placebo)}}$$

delta=difference with initial value.

The clinical evaluation of the test sites gives clear differences between the sites treated with placebo and with test substance. While sites treated with placebo give areas which are cherry-red, elevated and indurated, with compound A in 5% preparation (solution in 15% dimethylformamide, 42.5% ethanol and 42.5% propylene glycol) the treated areas can hardly be distinguished from the adjacent normal skin. They only show a slight reddish color. The difference in coloration can be clearly shown with the reflectometer. Dexamethasone shows in this model at the same concentration and in the same preparation only weak activity, for cyclossporin A no activity can be shown at all.

2. Determination of the activity after topical administration in the irritant-induced dermatitis model (mouse)

2.1. TPA-induced dermatitis:

Skin irritation with TPA in test animals is a method for testing substances as to their antiinflammatory activity after local application (Maibach, Lowe, Ed. *Models in Dermatology*, Vol. 3 [1987] p. 86–92, Karger-Basel). NMRI mice are given 10 µl of a TPA solution on the inner and outer side of the right pinna (2×10 µl/mouse=2×0.5 µg TPA/mouse). The left pinnae remain untreated. Treatment is effected 30 min. after irritation, by application of 2×10 µl of test solution onto the irritated ear surfaces, as described above. The evaluation of the test group is performed by comparison with a group where the right pinna has been treated with only the irritating solution and with the solvent used for the test substance. 6 hours after application of the irritant the animals are killed, the pinnae separated and weighed. The difference in weight of the two pinnae is used for the evaluation, whereby the individual differences of the test groups are statistically compared with the individual differences of the control groups (as under 1.1.). The activity of the test substances is indicated in % on the basis of the average values.

The results compared with indomethacin are reflected in Table 2. The solvent used is a mixture of dimethylacetamide, acetone and ethanol (2/4/4):

TABLE 2

| Substance | % concentration | % inhibition |
| --- | --- | --- |
| A | 3.6 | 56 |
|  | 1.2 | 52 |
| Indomethacin | 3.6 | 31 |
|  | 1.2 | 26 |

2.2. Dermatitis induced by croton oil

Croton oil is often used, as TPA, in order to induce an irritant-induced dermatitis on which substances can be tested for their anti-inflammatory activity (Maibach, Lowe, Ed., *Models in Dermatology*, Vol. 3 [1987] p. 86–92, Karger-Basel). NMRI-mice are given 15 µl of 0.23% croton oil (in a mixture of dimethylacetamide, acetone and ethanol 2/4/4) on the inner side of the right pinna. Treatment is effected simultaneously with the irritation, the test substance being dissolved in the solution of irritant applied at the auricular test site. Evaluation of the test group is performed by comparison of the inflammation with a group receiving only the irritant solution on the pinna. The animals are killed 6 hours after application of the irritant, the pinnae separated and weighed. The difference between the weights of the two individual pinnae is used for evaluation, by statistical comparison of the single differences in the test group with the single differences in the control group (as under 1.1.). The activity of the test substances is indicated in % based on average values.

The results obtained with compound A compared with indomethacin are shown in Table 3:

TABLE 3

| Substance | % concentration | % inhibition |
| --- | --- | --- |
| A | 3.6 | 85 |
|  | 1.2 | 64 |
|  | 0.4 | 52 |
| Indomethacin | 3.6 | 96 |
|  | 1.2 | 63 |
|  | 0.4 | 11 |

3. Inhibition of the oxidative burst in human polymorphonuclear neutrophil leUkocytes (inhibition of FMLP- or, respectively, A 23187-stimulated chemiluminescence):

Polymorphonuclear leukocytes (PMNL) are prepared from human peripheral blood (M. Schaude et al., *Mycoses* 31 (5) [1988] 259–267). Stock solutions of the test substances (500 mg/l) are freshly prepared on the day of experiment in 5% DMSO/RPMI 1640. For the determination of the chemiluminescence (CL) with Biolumal LB 9505 the luminescence indicator DMNH is used. The reaction mixture for determination of the CL of PMNL cells consists of 200 µl PMNL suspension (5×10$^6$ cells/ml), 100 µl of the respective test substance dilution or the solvent system as control and 25 µl of DMNH solution (2.5×10$^{-6}$M). The CL-reaction is started by addition of either 100 µl of the peptide FMLP (4×10$^{-6}$M) or of the calcium ionophor A 23187 (4×10$^{-6}$M). The CL reaction is measured at 37° at 20 seconds over a time span of 20 minutes. 3 parameters are used for evaluation of the results: peak intensity of the radiated light, time span up to the peak and surface area under the reaction curve. As minimal inhibiting concentration the concentration of test substance is chosen where a significant inhibition of all 3 parameters can be observed (Table 4).

TABLE 4

| Substance | MIC (μM) (FMLP) | MIC (μM) (A 23187) |
|---|---|---|
| A | 0.005 | 0.05 |
| B | 0.01 | 0.01 |
| C | 0.5 | 5 |
| D | <0.5 | 0.5 |
| E | <0.5 | 0.05 |

4. Inhibition of macrophage activation (inhibition of TPA-induced $PGE_2$ release)

Peritoneal exudate cells of NMRI mice pretreated 3 days earlier with 1.5 ml thioglycolate i.p. are harvested by peritoneal lavage, washed with deficient PBS and resuspended in DMEM medium supplemented with 10% FCS. 1×10⁶ cells are transferred to each well of a 24-wells plate, and the cells are left to adhere 4 hours at 37° and 5% $CO_2$. The cells are then washed twice with deficient PBS. The resultant, more than 95% pure macrophage population is stimulated with TPA (20 μl/1 hour) in DMEM-medium devoid of FCS. The conditioned media are centrifuged and the $PGE_2$ contents determined using a $^{125}$I-radioimmunotest. $PGE_2$-release inhibition with the test substances is measured as percentage inhibition compared to the controls.

The results are summarized in Table 5:

TABLE 5

| Substance | % inhibition at 1 μM |
|---|---|
| A | 30 |
| B | 60 |
| C | 60 |

5. Inhibition of proliferation of human keratinocytes

Cultures of human keratinocytes are obtained by trypsination of human foreskin from newborns or obtained as EpiPack from Clonetics Corp. (San Diego). The keratinocyte cultures are grown in culture flasks in a supplemented keratinocyte medium (KGM). The passages 3 to 5 of 80–90% confluent keratinocytes are resuspended in KGM at a concentration of 1×10⁵ cells/ml, and either 0.1 ml each of this cell suspension is added into a 96-wells microtiter plate or 1 ml each of this cell suspension are added into a 24-wells plate in the presence of test substance. The cells are grown for 48 hours at 37° and 5% $CO_2$. $^3$H-thymidine is incorporated during the last 16 hours (microtiter plate, 1 μCi/well), the cells are checked for their morphology, washed thrice with ice-cold, deficient PBS and twice with trichloroacetic acid, solubilized in 100 μl 10.1N NaOH containing 1% SDS, and the radioactivity is measured. Alternatively, cells from the 24-well plate are trypsinized (trypsin/EDTA), checked for viability by trypan blue exclusion, and triple aliquots are counted in a cell counter.

The result shows that compound A causes a dose-dependent reduction in proliferation in the concentration range from 0.5 to 5 μM (Table 6).

TABLE 6

| Substance | % inhibition compared to control |
|---|---|
| A 0.5 μM | 57 |
| A 1 μM | 74 |
| A 5 μM | 94 |
| Solvent | 0 |

| Abbreviations: | |
|---|---|
| DNFB | 2,4-dinitrofluorobenzene |
| DNCB | Dinitrochlorobenzene |
| TPA | 12-O-tetradecanoylphorbol-13-acetate |
| $PGE_2$ | prostaglandin E2 |
| FMLP | N-formyl-L-methionyl-L-leucyl-L-phemylalanine |
| DTH | delayed-type hypersensitivity |
| A 23187 | calcium ionophor |
| DMSO | dimethylsulfoxide |
| DMNH | 7-dimethylaminonaphthalene-1,2-dicarboxylic acid hydrazide |
| PMNL | polymorphonuclear leukocytes |
| CL | chemiluminescence |
| MIC | minimal inhibitory concentration |
| PBS | phosphate-buffered saline |
| FCS | fetal calf serum |
| SDS | sodium dodecylsulphate |

Compound A (FK 506):

17-Allyl-1,14-dihydroxy-12-[2-(4-hydroxy-3-methoxycyclohexyl)-1-methylvinyl]-23,25-dimethoxy-13,19,21,27-tetramethyl-11, 28-dioxa-4-azatricyclo[22.3.1.0$^{4,}$ $^9$]octacos-18-ene-2,3,10,16-tetraone (disclosed on page 32 in EP 184 162)

($R^1$ $R^2$=OH; $R^3$=allyl; n=2; single bond);

Compound B (dihydro-FK 506):

1,14-dihydroxy-12-[2-(4-hydroxy-3-methoxycyclohexyl)-1-methylvinyl]-23,25-dimethoxy-13,19,21,27-tetramethyl-17-propyl-11,28-dioxa-4-azatricyclo[22.3.1.0$^{4,9}$]octacos-18-ene-2,3,10,16-tetraone (disclosed on page 98 as Example 21 in EP 184 162)

($R^1$, $R^2$=OH; $R^3$=n-propyl; n=2; single bond);

Compound C (dehydrated-FK 506):

17-allyl-1-hydroxy-12-[2-(4-hydroxy-3-methoxycyclohexyl)-1-methylvinyl]-23,25-dimethoxy-13, 19,21,27-tetramethyl-11,28-dioxa-4-azatricyclo[22.3.1.0$^{4,}$ $^9$]octacosa-14,18-diene-2,3,10,16-tetraone (disclosed on page 95 as part of Example 17 in EP 184 162)

($R^1$=OH; $R^2$=H; $R^3$=allyl; n=2; double bond);

Compound D (diacetyl-FK 506):

14-acetoxy-12-[2-(4-acetoxy-3-methoxycyclohexyl)-1-methylvinyl]-17-allyl-1-hydroxy-23,25-dimethoxy-13,19, 21,27-tetramethyl-11,28-dioxa-4-azatricyclo[22.3.1.0$^{4,}$ $^9$]octacos-18-ene-2,3,10,16-tetraone (disclosed on page 89 as part of Example 6 in EP 184 162)

($R^1$ $R^2$=acetoxy; $R^3$–allyl; n=2; single bond);

Compound E (monoacetyl-FK 506):

12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$^{4,}$ $^9$]octacos-18-ene-2,3,10,16-tetraone (disclosed on page 88 as Example 5 in EP 184 162)

($R^1$=acetoxy; $R^2$=hydroxy; $R^3$=allyl; n=2; single bond).

Compound A (FK 506) is a product isolated from nature. It has a definite stereochemical configuration. However, even though it is disclosed in EP 184 162 with extensive characterization data, the formula given on page 32 in EP 184 162 for FK 506 does not indicate any stereochemical configuration. There is further no indication on the precise configuration of any compound specifically disclosed in EP 184 162. Since there are many asymmetry centers the formula on page 32 thus covers many potential compounds, but only one of them correspnds to FK 506. The exact configuration for FK 506 has been published subsequently, e.g. in H. Tanaka et al., *J. Am. Chem. Soc.* 109 (1987) 5031–5033, T. Kino et al., *J. Antibiotics* 40 (1987)

1249–1255 and T. Taga et al., *Acta Cryst.* C43 (1987) 751–753, and appears to be as follows:

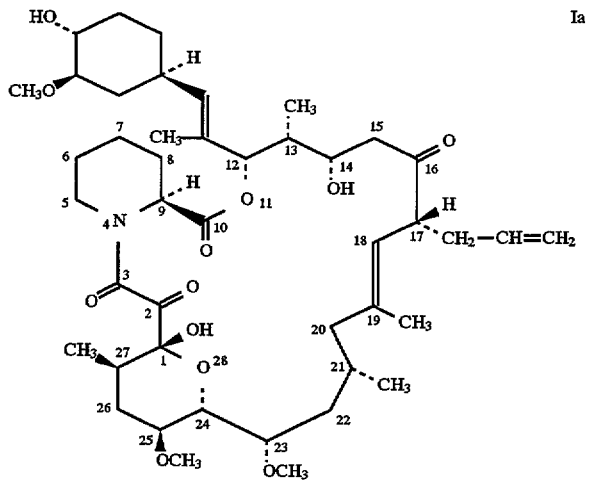

By implication, since in EP 184 162 the preparation of compounds B, C, D and E is effected starting from FK 506 and using reaction steps which do not modify the configuration, compounds B, C, D and E also have a configuration corresponding to that shown above for compound A.

An aspect of the invention is thus the use of the compounds of formula I in free form or in pharmaceutically acceptable salt form in the topical treatment of inflammatory and hyperproliferative skin diseases and of cutaneous manifestations of immunologically-mediated illnesses, such as: psoriasis, atopical dermatitis, contact dermatitis and further eczematous dermatitises, seborrhoeic dermatitis, *Lichen planus*, Pemphigus, bullous Pemphigoid, Epidermolysis bullosa, urticaria, angioedemas, vasculitides, erythemas, cutaneous eosinophilias, Lupus erythematosus and Alopecia arcata.

Preferred are the compounds of formula I wherein $R^1$, $R^2$ and n are as defined above for formula I, $R^3$ is propyl or allyl and the symbol of a line and dotted line is a single bond in particular, the compound wherein $R^1$ and $R^2$ are hydroxy, $R^3$ is allyl, n is 2, and the symbol of a line and dotted line is a single bond; especially preferred is compound A.

For the above use the dosage to be administered is of course dependent on the compound to be administered, the mode of administration and the type of treatment. Satisfactory results are obtained in larger mammals with local administration of a 1–3% concentration of active substance several times daily, e.g. 2 to 5 times daily. Examples of indicated galenical forms are lotions, gels and-creams.

A further aspect of the invention is a pharmaceutical composition for the above topical uses, containing a compound of formula I in free form or in pharmaceutically acceptable salt form, together with a pharmaceutically acceptable carrier or diluent.

We claim:

1. A method of topically treating inflammatory or hyperproliferative skin diseases or cutaneous manifestations of immunologically-mediated illnesses, in a mammal in need of said treatment, which comprises administering topically to said mammal in an amount effective for the treatment of inflammatory or hyperproliferative skin diseases or cutaneous manifestations of immunologically mediated illnesses a compound of formula I wherein
$R^1$ is optionally protected hydroxy,
$R^2$ is hydrogen or optionally protected hydroxy,
$R^3$ is methyl, ethyl, propyl or allyl,
n is 1 or 2 and
the symbol of a line and dotted line is a single bond or a double bond,
in free form or in pharmaceutically acceptable salt form.

2. A method according to claim 1, wherein
$R^3$ is propyl or allyl,
in free form or in pharmaceutically acceptable salt form.

3. A method according to claim 1,
wherein $R^1$ and $R^2$ are hydroxy,
$R^3$ is allyl,
n is 2, and
the symbol of a line and dotted line is a single bond,
in free form.

4. A method according to claim 1 in which the compound is

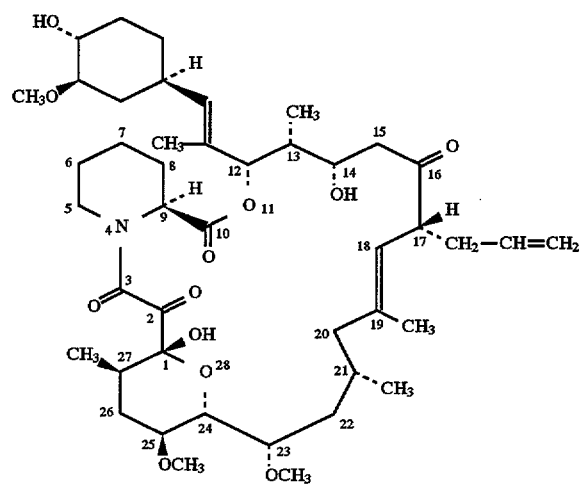

in free form.

5. A method according to claim 1 in which the compound is administered 2 to 5 times daily in the form of a lotion, gel, or cream comprising 1 to 3% of the compound.

6. A method of topically treating atopical dermatitis, contact dermatitis, eczematous dermatitises, seborrhoeic dermatitis, *Lichen planus, Pemphigus, bullous* Pemphigoid, Epidermolysis bullosa, urticaria, angioedemas, vasculitides, erythemas, cutaneous eosinophilias, or Alopecia areata in a mammal in need of said treatment, which comprises administering topically to said mammal in an amount effective for the treatment of atopical dermatitis, contact dermatitis, eczematous dermatitises, seborrhoeic dermatitis, Lichen planus, Pemphigus, bullous Pemphigoid, Epidermolyeis bulloea, urticaria, angioedemaes, vasculitides, erythomas, cutaneous eosinophilias, or Alopecia areata a compound of formula I wherein $R^1$ is optionally protected hydroxy, $R^2$ is hydrogen or optionally protected hydroxy, $R^3$ is methyl ethyl, propyl or allyl, n is 1 or 2 and the symbol of a line and dotted line is a single bond or a double bond, in free form or in pharmaceutically acceptable salt form.

7. A method according to claim 6, wherein $R^3$ is propyl or allyl, in free form or in pharmaceutically acceptable salt form.

8. A method according to claim 6, wherein $R^1$ and $R^2$ are hydroxy, $R^3$ is allyl, n is 2, and the symbol of a line and dotted line is a single bond, in free form.

9. A method according to claim 6 in which the compound is in free form.

10. A method according to claim 6 in which the compound is administered 2 to 3 times daily in the form of a lotion, gel, or cream comprising 1 to 3% of the compound.

11. A method of topically treating atopical dermatitis, contact dermatitis, eczematous dermatitises, or seborrhoeic dermatitis in a mammal in need of said treatment, which comprises administering topically to said mammal in an amount effective for the treatment of atopical dermatitis, contact dermatitis, eczematous dermatitises, or seborrhoeic dermatitis a compound of formula I wherein $R^1$ is optionally protected hydroxy, $R^2$ is hydrogen or optionally protected hydroxy, $R^3$ is methyl, ethyl, propyl or allyl, n is 1 or 2 and the symbol of a line and dotted line is a single bond or a double bond, in free form or in pharmaceutically acceptable salt form.

12. A method according to claim 11, wherein $R^3$ is propyl or allyl in free form or in pharmaceutically acceptable salt form.

13. A method according to claim 11, wherein $R^1$ and $R^2$ are hydroxy, $R^3$ is allyl, n is 2, and the symbol of a line and dotted line is a single bond, in free form.

14. A method according to claim 11 in which the compound is

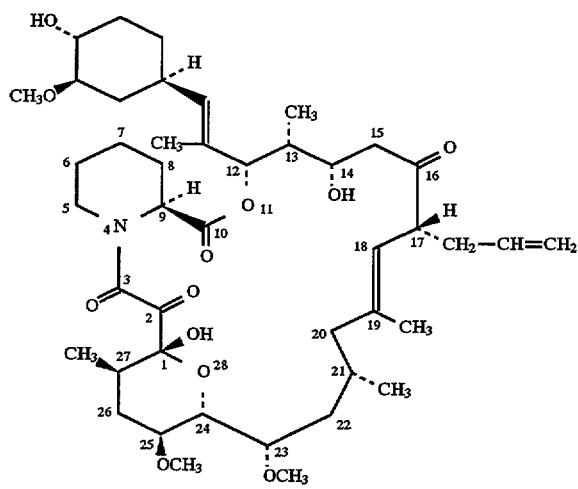

in free form.

15. A method according to claim 11 in which the compound is administered 2 to 5 times daily in the form of a lotion, gel, or cream comprising 1 to 3% of the compound.

16. A method according to claim 11 of topically treating atopical dermatitis.

17. A method according to claim 11 of topically treating contact dermatitis or eczematous dermatitises.

18. A method according to claim 11 of topically treating seborrhoeic dermatitis.

* * * * *